United States Patent
Hwang

(10) Patent No.: US 8,150,504 B2
(45) Date of Patent: Apr. 3, 2012

(54) LOCAL BODY FAT MEASUREMENT DEVICE AND METHOD OF OPERATING THE SAME

(75) Inventor: Jin Sang Hwang, Suwon-si (KR)

(73) Assignee: Samsung Electronics Co., Ltd., Suwon-Si (KR)

( * ) Notice: Subject to any disclaimer, the term of this patent is extended or adjusted under 35 U.S.C. 154(b) by 988 days.

(21) Appl. No.: 11/601,634

(22) Filed: Nov. 20, 2006

(65) Prior Publication Data

US 2007/0239070 A1    Oct. 11, 2007

(30) Foreign Application Priority Data

Mar. 27, 2006   (KR) .................. 10-2006-0027404

(51) Int. Cl.
  *A61B 5/05*   (2006.01)
  *A61B 6/00*   (2006.01)
  *A61B 5/103*  (2006.01)
  *A61B 5/117*  (2006.01)

(52) U.S. Cl. .................. 600/547; 600/473; 600/587

(58) Field of Classification Search .................. 600/473, 600/547, 587
See application file for complete search history.

(56) References Cited

U.S. PATENT DOCUMENTS

| | | | |
|---|---|---|---|
| 4,850,365 A | 7/1989 | Rosenthal | |
| 4,928,014 A | 5/1990 | Rosenthal | |
| 5,014,713 A * | 5/1991 | Roper et al. | 600/473 |
| 5,941,825 A | 8/1999 | Lang et al. | |
| 6,285,904 B1 * | 9/2001 | Weber et al. | 600/473 |
| 6,618,615 B1 | 9/2003 | Kimura et al. | |
| 6,985,767 B2 * | 1/2006 | Horiuchi et al. | 600/476 |
| 7,203,536 B2 * | 4/2007 | Masuo | 600/547 |
| 2003/0176808 A1 * | 9/2003 | Masuo | 600/547 |
| 2004/0002662 A1 | 1/2004 | Hjelt et al. | |
| 2004/0059242 A1 | 3/2004 | Masuo et al. | |
| 2005/0020936 A1 | 1/2005 | Lin | |
| 2005/0075549 A1 * | 4/2005 | Kondoh et al. | 600/323 |

FOREIGN PATENT DOCUMENTS

| | | |
|---|---|---|
| EP | 0 516 251 | 3/1992 |
| JP | 2000-229072 | 8/2000 |
| JP | 2001-211238 | 8/2001 |
| JP | 2001-321350 | 11/2001 |
| JP | 2001-321351 | 11/2001 |
| JP | 2001-346784 | 12/2001 |
| KR | 0161602 | 1/1999 |
| KR | 2001-0099267 | 11/2001 |
| KR | 2001-0099762 | 11/2001 |
| KR | 2001-99762 | 11/2001 |
| KR | 1020010106960 | 12/2001 |
| KR | 1020020011730 | 2/2002 |
| KR | 20-0318855 | 6/2003 |
| KR | 1020040003255 | 1/2004 |

(Continued)

*Primary Examiner* — Max Hindenburg
*Assistant Examiner* — Adam Eiseman
(74) *Attorney, Agent, or Firm* — Staas & Halsey LLP

(57) ABSTRACT

A method of operating a local body fat measurement device including: measuring a body fat thickness of the at least one predetermined measurement point of the predetermined anatomical area; displaying a measured body fat thickness at each measurement point on a output device; and maintaining a memory device storing a local body fat measurement table storing the at least one measurement point. The local body fat measurement table comprises an anatomical area image portraying a shape of the predetermined anatomical area, and the at least one measurement point is displayed in the anatomical area image.

12 Claims, 8 Drawing Sheets

FOREIGN PATENT DOCUMENTS

| | | |
|---|---|---|
| KR | 1020040032451 | 4/2004 |
| KR | 1020040106833 | 12/2004 |
| KR | 1020050027368 | 3/2005 |
| KR | 10-2005-0071841 | 7/2005 |
| KR | 1020050073730 | 7/2005 |
| KR | 1020050099444 | 10/2005 |
| KR | 1020050103355 | 10/2005 |
| KR | 1020050105783 | 11/2005 |
| KR | 1020050105822 | 11/2005 |

* cited by examiner

FIG. 3

| ANATOMICAL AREA \ MEASUREMENT POINT | | TOP | BOTTOM | LEFT | RIGHT | N | N+1 |
|---|---|---|---|---|---|---|---|
| CHEEK (FACE) | LEVEL 1 | | | ○ | ○ | | |
| | LEVEL 2 | ○ | ○ | ○ | ○ | | |
| FOREARM | LEVEL 1 | ○ | ○ | ○ | ○ | | |
| | LEVEL 2 | ○ | ○ | ○ | ○ | ○(BOTTOM LEFT) | ○(BOTTOM RIGHT) |
| ABDOMEN | LEVEL 1 | | | ○ | ○ | CENTER | |
| | LEVEL 2 | LEFT45° | RIGHT45° | ○ | ○ | CENTER | |
| | LEVEL 3 | LEFT30° | RIGHT30° | ○ | ○ | CENTER | LEFT60° RIGHT60° |
| THIGH | LEVEL 1 | ○ | ○ | ○ | ○ | | |
| | LEVEL 2 | ○ | ○ | ○ | ○ | ○(BOTTOM LEFT) | ○(BOTTOM RIGHT) |
| CALF | LEVEL 1 | | ○ | ○ | ○ | | |
| | LEVEL 2 | | ○ | ○ | ○ | ○(BOTTOM LEFT) | ○(BOTTOM RIGHT) |

300

600

YOU HAVE KNOCKOUT BODY.
KEEP YOURSELF FIT BY STEADY
EXERCISE.

2006. 2. 28

| LEFT | 45 | 90 | 90 | 45 | RIGHT |
|------|-----|-----|-----|-----|-------|
| 2mm  | 3mm | 5mm | 4mm | 3mm | 1mm   |
| 0    | 0   | 0   | 0   | 0   | 0     |

BMI= 20

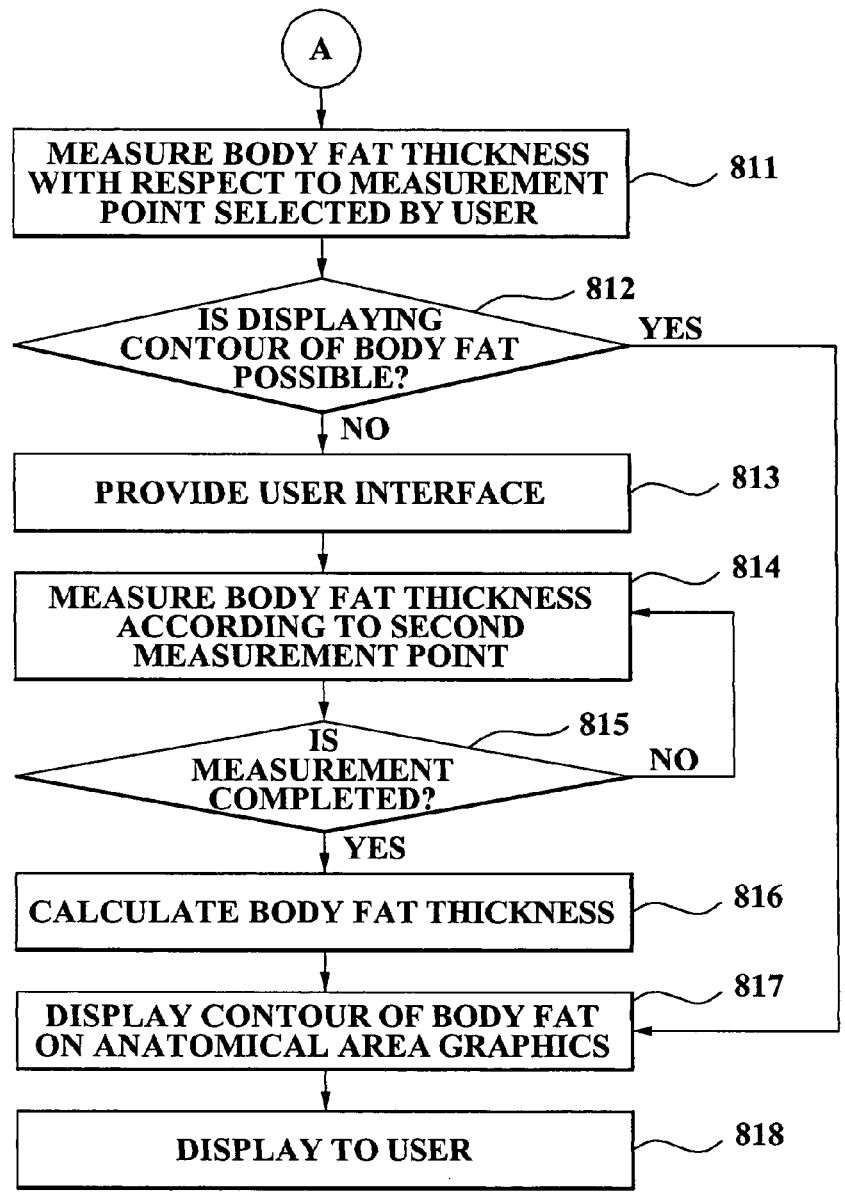

LOCAL BODY FAT MEASUREMENT DEVICE AND METHOD OF OPERATING THE SAME

CROSS-REFERENCE TO RELATED APPLICATION

This application claims the benefit of Korean Patent Application No. 10-2006-0027404, filed on Mar. 27, 2006, in the Korean Intellectual Property Office, the disclosure of which is incorporated herein by reference.

BACKGROUND OF THE INVENTION

1. Field of the Invention

The present invention relates to a local body fat measurement device and a method of operating the same, and more particularly, to a local body fat measurement device and the method of operating the same, which measures an amount of body fat of an anatomical area that a user wants to measure, and displays a graphical image displaying a thickness of body fat of the anatomical area so that the user may recognize a degree of the user's obesity with respect to the user's particular anatomical area so as to increase an effect of a diet.

2. Description of Related Art

Ubiquitous technology represents an information-communication environment where a user may freely access a network regardless of location without considering the network and a computer. When Ubiquitous technology becomes commercialized, people may freely use information technology (IT) in a myriad of diverse locations, such as at home, in a car, as well as at a top of a mountain. Also, commercialization of Ubiquitous technology may increase a number of computer users accessing the network, and expand the IT industry according to the increase. Due to portability, convenience and the utility that such access to networks provides regardless of time and location, competition to develop Ubiquitous technology is currently fierce around the world.

Ubiquitous-related technology may be applied to many areas of a human life. Ubiquitous-HealthCare (hereinafter, U-HealthCare) has recently been in the spotlight as a notable technology area due to the 'well-being' boom. U-HealthCare means Ubiquitous technology which enables anyone to readily receive medical services at any time and at any place by installing medical service-related chips or sensors in places of the user's living space. With U-HealthCare, various types of medical attention, such as physical examinations, disease management, emergency care, consultation with a doctor and the like, which currently are only performed in hospitals, may be naturally integrated into our daily lives, thus may be accomplished without going to a hospital.

Currently, people who are obese or are overweight due to advancement in their standard of living and lack of exercise due to the same is increasing. Obesity and being overweight may cause many kinds of adult diseases, and many kinds of discrimination in social life may occur due to these conditions. Accordingly, people are highly interested in a diet, and treatment and prevention of these conditions, thereby rapidly expanding a scale of industries associated with the obesity. One of the main indicators indicating a degree of obesity or of being overweight is body fat representing an amount of a fat in a human body. One may recognize a degree of his or her obesity by measuring a body fat thickness of his or her own and may go on a diet.

Currently, portable body fat measurement devices are in the spotlight as a part of U-HealthCare due to a 'diet' boom. In the past, the body fat thickness was measured only in hospitals or various kinds of clinics. However, currently, the body fat thickness may be measured at any time and at any place through portable body fat measurement devices. Accordingly, a more effective diet becomes possible.

Lots of people today are obese or overweight. Particularly, students and office workers, as well others with sedentary professions, are generally susceptible to these conditions because of a high proportion of caloric intake compared to caloric expenditure through exercise. Accordingly, students and office workers are susceptible to a localized obesity, particularly, an abdominal obesity due. However, a conventional portable body fat measurement device mostly provides a function of measuring the amount of body fat of a body. Accordingly, when only a particular anatomical area such as an abdomen is obese and other anatomical areas are normal, the user may not precisely measure and recognize the degree of his or her abdominal obesity.

Specifically, to respectively measure the body fat with respect to an anatomical area, and to effectively cope with the local obesity for with the conventional portable body fat measurement device are impossible. Accordingly, a development of a local body fat measurement device which respectively measures the body fat with respect to the anatomical area, and provides anatomical area image visually displaying the body fat thickness of the measured anatomical area is required, so that the user may recognize a degree of his or her obesity with respect to the predetermined anatomical area more clearly, and an effect of a diet is increased.

BRIEF SUMMARY

An aspect of the present invention provides a local body fat measurement device and a method of operating the same, which provides a display screen in which a predetermined anatomical area is illustrated to a user and induces the user to measure body fat of at least one measurement point of the anatomical area through the display screen, so that the user may measure a thickness of body fat of the anatomical area more conveniently.

An aspect of the present invention also provides a local body fat measurement device and a local body fat measurement method, which displays to a user a predetermined display screen that displays a contour of body fat which is generated by using a measured body fat thickness of the anatomical area, so that the user may recognize the user's degree of obesity more easily, and increase an effect of a diet.

According to an aspect of the present invention, there is provided a method of operating a local body fat measurement device, the method including: measuring a body fat thickness of the at least one predetermined measurement point of the predetermined anatomical area; displaying a measured body fat thickness at each measurement point on a output device; and maintaining a memory device storing a local body fat measurement table storing the at least one measurement point. The local body fat measurement table comprises an anatomical area image portraying a shape of the predetermined anatomical area, and the at least one measurement point is displayed in the anatomical area image.

According to an aspect of the present invention, there is provided a method of operating a local body fat measurement device, the method including: providing a user interface inducing measurement of body fat of at least one predetermined measurement point on a predetermined anatomical area; measuring body fat thickness at each measurement point; and displaying each first fat thickness measure on anatomical area image portraying a shape of the predetermined anatomical area.

According to an aspect of the present invention, there is provided a method of operating a local body fat measurement device, the method including: measuring body fat thickness of at least one first measurement point on a predetermined anatomical area selected by a user; and providing a user interface inducing measurement of body fat thickness of at least one predetermined second measurement point, when displaying each first body fat thickness measure, and when indicating that display of the measured thickness is impossible.

According to another aspect of the present invention, there is provided a local body fat measurement device including: a measurement leading unit inducing measurement of body fat of at least one predetermined measurement point of a predetermined anatomical area; a local body fat measurement unit measuring body fat thickness at each measurement point; a graphics control unit controlling a display of each body fat thickness measure on an output device; and a memory device storing a local body fat measurement table including the at least one measurement point. The local body fat measurement table comprises an anatomical area image portraying a shape of the predetermined anatomical area, and the at least one measurement point is displayed in the anatomical area image.

According to another aspect of the present invention, there is provided a local body fat measurement device, including: a sensor sending a measurement signal to at least one measurement point of an anatomical area of a body, receiving a reflected signal therefrom, and converting the received reflected signal into an electrical signal; a low band pass filter extracting a low frequency element of the converted electrical signal; an analog to digital (A/D) converter converting the extracted low frequency element into a digital signal; a central processing unit (CPU) receiving the converted low frequency element and measuring a body fat thickness of the body at the at least one measurement point based on an intensity of the reflected signal; a memory device storing a local body fat measurement table including the at least one measurement point, the local body fat measurement table comprising an anatomical area image portraying a shape of the anatomical area; and a display displaying results of the body fat measurement by displaying on the anatomical area image each body fat measure at each corresponding measurement point.

A method of operating a local body fat measurement device, including: inputting a selection of an anatomical area where a body fat thickness is to be measured; determining whether at least one predetermined measurement point of the anatomical area is to be displayed and, providing a user interface displaying the at least one measurement point when the at least one measurement point is to be displayed; measuring body fat at each measurement point; calculating body fat thickness of each measurement point and storing each body fat thickness measurement; and displaying a contour of body fat of the anatomical area by displaying each body fat measure on an anatomical area image at each measurement point, the anatomical area image portraying a shape of the anatomical area.

Additional and/or other aspects and advantages of the present invention will be set forth in part in the description which follows and, in part, will be obvious from the description, or may be learned by practice of the invention.

BRIEF DESCRIPTION OF THE DRAWINGS

The above and/or other aspects and advantages of the present invention will become apparent and more readily appreciated from the following detailed description, taken in conjunction with the accompanying drawings of which:

FIG. 3 is a diagram illustrating a local body fat measurement table according to an embodiment of the present invention;

FIG. 8 is a flowchart illustrating a flow of a method of operating a local body fat measurement device according to a second example of an embodiment of the present invention.

DETAILED DESCRIPTION OF EMBODIMENTS

Figure 1:
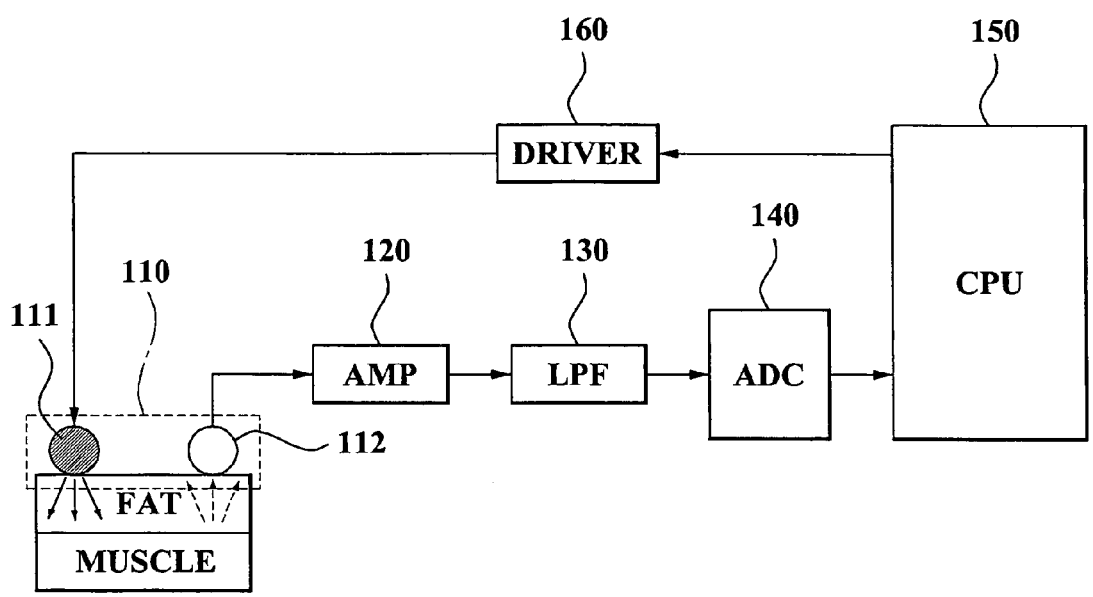
FIG. 1 is a block diagram illustrating a configuration of a local body fat measurement device using near infrared rays according to an embodiment of the present invention.

Reference will now be made in detail to embodiments of the present invention, examples of which are illustrated in the accompanying drawings, wherein like reference numerals refer to the like elements throughout. The embodiments are described below in order to explain the present invention by referring to the figures.

Generally, a hydrodensitometry, a bioelectrical impedance analysis (BIA), a ultrasound assessment of fat, an arm X-ray assessment of fat, a near infrared (NIR) absorption assessment of fat, etc. are examples of body fat measurement methods.

Among the above-mentioned measurement methods, the NIR absorption assessment of fat is widely used due to convenience. In the near infrared absorption assessment of fat, body fat is measured by using a theory in which an NIR ray is irradiated to in-vivo tissue, and is reflected from the in-vivo tissue. The body fat may be more precisely and simply measured by using the NIR absorption assessment of fat. Accordingly, as an example, a case where the body fat is measured according to the NIR absorption assessment of fat will be described in this specification. However, it is to be understood that this is a non-limiting example for explanatory purposes only. Indeed, it is to be understood that embodiments of the present invention are applicable to other body fat measuring methods.

FIG. 1 is a block diagram illustrating a configuration of a local body fat measurement device using NIR rays according to an embodiment of the present invention.

As illustrated in FIG. 1, the local body fat measurement device according to the present embodiment includes a near infrared sensor 110 including a light-emitting sensor 111, and a light-receiving sensor 112, an amplifier 120, a low band pass filter 130, an analog to digital (A/D) converter 140, a central processing unit (CPU) 150, and a driver 160.

When the light-emitting sensor 111 irradiates a NIR ray to a body of a user according under control of the CPU 150 and the driver 160, a part of the NIR ray is absorbed into the body and a remainder the NIR ray is reflected by the body and received and focused by the light-receiving sensor 112.

The received NIR ray is condensed in the light-receiving sensor 112 and is converted to an electric signal, amplified through the amplifier 120, and transmitted to the low-pass filter 130. A low frequency element of the NIR ray signal is extracted through the low-pass filter 130. The low frequency element of the NIR ray is converted into a digital signal through the A/D converter 140 and then transmitted to the CPU 150.

The CPU 150 calculates an intensity of the portion of the NIR ray reflected from the body through the low frequency element of the reflected NIR ray signal which is converted to the digital signal. The CPU 150 calculates a proportion of the intensity of the reflected NIR ray and an intensity of the NIR ray irradiated by light-emitting sensor 111. Accordingly, the CPU 150 may calculate a body fat thickness of the body.

The local body fat measurement device according to the present embodiment may measure the body fat thickness with respect to an anatomical area of the user by performing the above operation.

As illustrated in FIG. 1, the local body fat measurement device according to the present embodiment may be a dedicated device performing only the body fat measurement. However, the local body fat measurement device according to the present embodiment may also be a part of a portable device, such as a personal digital assistant (PDA), a mobile phone, a personal communication service (PCS) phone, a hand-held personal computer (hand-held PC), a code division multiple access (CDMA)-2000 (1X, 3X) phone, a wideband code division multiple access (wideband CDMA) phone, a dual band/dual mode phone, a Global System for Mobile Communications (GSM) phone, a mobile broadband system (MBS) phone, or a satellite/terrestrial digital multimedia broadcasting (DMB) phone, an Moving Picture Experts Group (MPEG) Audio-Layer 3 (MP3) player, a portable multimedia player (PMP), a portable game player, a notebook PC, and the like.

Hereinafter, an example of the local body fat measurement device according to the present embodiment as a part of a portable device will be described.

Figure 2:
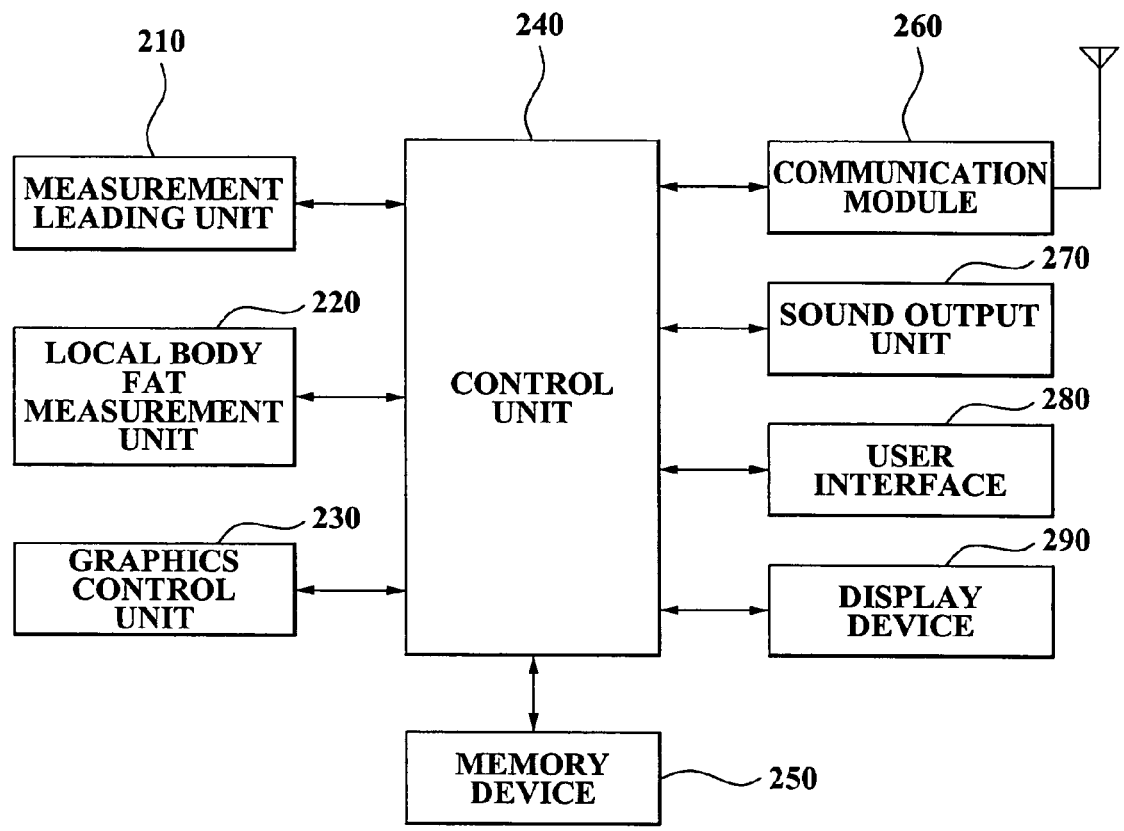
FIG. 2 is a block diagram illustrating a configuration of a portable terminal including a configuration of a local body fat measurement device according to an embodiment of the present invention.

FIG. 2 is a block diagram illustrating a configuration of a portable terminal including a configuration of a local body fat measurement device according to an embodiment of the present invention.

The local body fat measurement device according to an embodiment of the present invention may include a measurement leading unit 210, a local body fat measurement unit 220, a graphics control unit 230, a control unit 240, a memory device 250, a communication module 260, a sound output unit 270, a user interface 280, and a display device 290.

Figure 4:
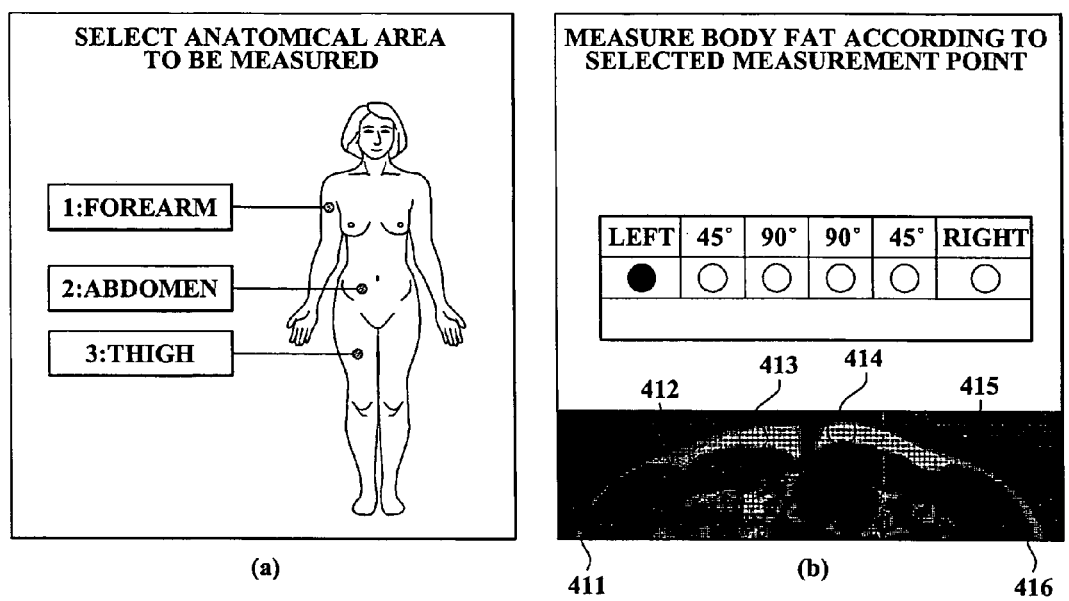
FIGS. 4(a) and 4(b) are diagrams illustrating a display screen inducing a local body fat measurement by using anatomical area images according to an embodiment of the present invention.

When a user inputs a command to make a local body fat measurement of a predetermined anatomical area through the user interface 280, the measurement leading unit 210 induces the user to measure a body fat in at least one predetermined measurement point of the anatomical area. In this instance, the measurement leading unit 210 may load and display on the display device 290 a local body fat measurement table which is stored in the memory device 250. A local body fat measurement operation of the measurement leading unit 210 by using the local body fat measurement table will be described by referring to FIGS. 3 and 4.

FIG. 3 is a diagram illustrating a local body fat measurement table according to an embodiment of the present invention.

As illustrated in FIG. 3, at least one measurement point corresponding to at least one anatomical area of a user may be respectively stored in the local body fat measurement table according to an embodiment of the present invention. As an example of the anatomical area, a face including a cheek, a forearm, an abdomen, a thigh, and a calf may be measured. Also, at least one measurement level may be recorded according to a measurement point of the respective anatomical area.

As an example, in the case of an abdomen as illustrated in FIG. 3, in a level 1, measurement points with respect to a left, a right, and a center of the abdomen may be set. Also, in a level 2, the left, the measurement points with respect to the left, a left 45°, the center, a right 45°, and the right of the abdomen may be set. In a level 3, measurement points with respect to the left, a left 30°, a left 60°, the center, a right 60°, a right 30°, and the right of the abdomen may be set.

The measurement leading unit 210 of FIG. 2 may induce the user to measure body fat of at least one measurement point stored in the local body fat measurement table with respect to the anatomical area selected by the user. The measurement leading unit 210 may control anatomical area images which the anatomical area and at least one measurement point included in the anatomical area are to be displayed on a display device 290. Specifically, the anatomical area images may be recorded in a memory device 250 of FIG. 2 included in the local body fat measurement table 300. An inducement of a body fat measurement by using the anatomical area images will be described in detail by referring to FIGS. 4(a) and 4(b).

FIGS. 4(a) and 4(b) are diagrams illustrating a display screen inducing a local body fat measurement by using anatomical area images according to an embodiment of the present invention.

As described above, a measurement leading unit 210 of FIG. 2 may extract the anatomical area image(s) corresponding to the anatomical area selected by a user from a memory device 250 of FIG. 2 and cause the extracted anatomical area images to be displayed on a display device 290 of FIG. 2. For example, when the user selects the user's abdomen as a measurement point, as illustrated in FIG. 4(b), the measurement leading unit 210 may display a local body fat measurement table of the abdomen together with anatomical area image(s) where a cross section of the abdomen is illustrated.

In this instance, as an example, when the user selects a level 2 among an abdomen measurement level of a local body fat measurement table 300 illustrated in FIG. 3, the measurement leading unit 210 of FIG. 2 may induce the user to measure a body fat at a left measurement point 411, a left 45° measurement point 412, a left center measurement point 413, a right center measurement point 414, a right 45° measurement point 415, and the right measurement point 416. For example, when a body fat measurement at the left measurement point 411 is induced, the measurement leading unit 210 may highlight the left measurement point 411 of the abdominal area graphics or display the left measurement point 411 of the anatomical area images of the abdomen to be flashing.

Referring again to FIG. 2, according to an inducement of a body fat measurement according at each measurement point, when the user tries to measure body fat, a local body fat measurement unit 220 measures body fat thickness at each measurement point. The measured body fat thickness at each measurement point may be stored in the memory device 250 corresponding to the respective measurement point.

The graphics control unit 230 generates a display screen portraying the body fat thickness of the anatomical area by using the body fat thickness value at each respective measurement point and provides the same to the display screen.

Specifically, the graphics control unit 230 may cause the display of the body fat thickness point corresponding to the respective measurement point on the anatomical area images by using the body fat thickness which is measured by the local body fat measurement unit 220 at each respective measurement point. Then, the graphics control unit 230 may display a contour of the body fat on the anatomical area images by linking the body fat thickness points to each other, which is displayed on the anatomical area images or using a cosine interpolation with respect to the body fat thickness. Further detailed description of the process will follow referring to FIGS. 5 and 6.

Figure 5:
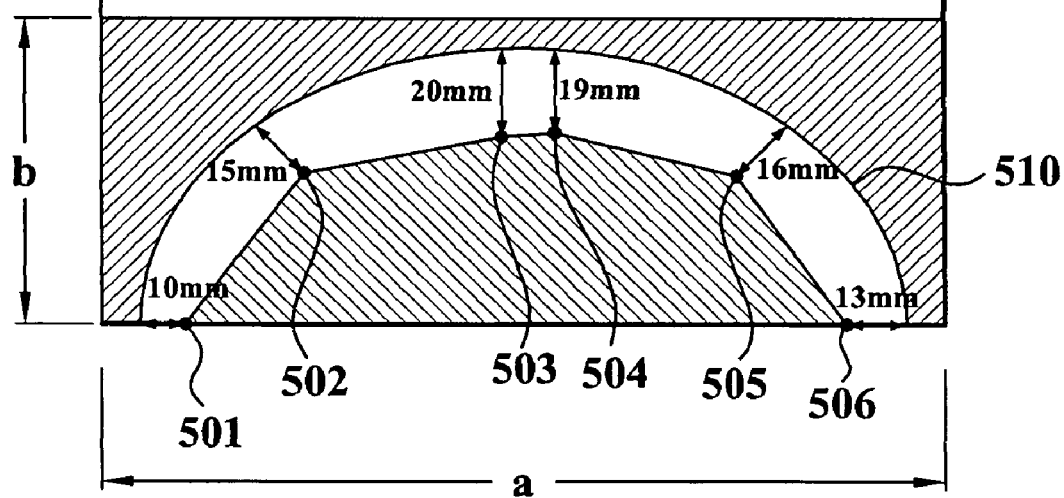
FIG. 5 is a diagram illustrating a display screen displaying anatomical area images in which a contour of body fat is displayed by linearly linking body fat thickness points to each other according to an embodiment of the present invention.

FIG. 5 is a diagram illustrating a display screen displaying anatomical area images which a contour of body fat is displayed by linearly linking the body fat thickness points to each other according to an embodiment of the present invention.

Like the above example, when a user selects the user's abdomen as a measurement point, for example, a local body fat measurement unit 220 of FIG. 2 may respectively measure a body fat thickness of 10 mm with respect to a left measurement point, a body fat thickness of 15 mm with respect to a left 45° measurement point, a body fat thickness of 20 mm with respect to a left center measurement point, a body fat thickness of 19 mm with respect to a right center measurement point, a body fat thickness of 16 mm with respect to a right 45° measurement point, and a body fat thickness of 13 mm with respect to the right measurement point of the abdomen. As illustrated in FIG. 5, the measured respective body fat thickness may be displayed in a form of a local body fat measurement table on a display screen 500 according to a control of a control unit 240.

The graphics control unit 230 of FIG. 2 may cause the display of a contour of body fat on the anatomical area image(s) by using each body fat thickness measure. Specifically, the graphics control unit 230 may cause the display of a left body fat thickness point 501 perpendicularly spaced apart from the left measurement point of an abdominal contour 510 by about 15 mm in the anatomical area images. Also, the graphics control unit 230 may respectively display a left 45° body fat thickness point 502 perpendicularly spaced apart from the left 45° measurement point by about 15 mm, a left center body fat thickness point 503 perpendicularly spaced apart from the left center measurement point by about 20 mm, a right center body fat thickness point 504 perpendicularly spaced apart from the right center measurement point by about 19 mm, a right 45° body fat thickness point 505 vertically spaced apart from the right 45° measurement point by about 16 mm, and a right body fat thickness point 506 perpendicularly spaced apart from the right measurement point by about 13 mm.

Next, the graphics control unit 230 may cause the display of the contour of the body fat by linearly linking each body fat thickness measure points each other, when there are multiple points. Accordingly, the user may easily recognize a degree of his or her abdominal obesity by seeing an abdominal area graphics which the contour of the user's body fat is displayed.

In the display screen 500 illustrated in FIG. 5, the abdominal contour 510 of the abdominal area graphics may be set to a width a and a height b according to a physical characteristic of the user. In this instance, the local body fat measurement device according to the present invention may receive a physical characteristic data of the user from the user in advance, and store and maintain the physical characteristic data in the memory device 250.

As an example, a body mass index (BMI) may be applied to the physical characteristic data of the user. According to the BMI assessment, when a height of the user is 170 cm, and a weight of the user is 75 kg, a BMI score of the user is 75/1.70/1.70=25.95. The BMI score indicates that the user may be considered to be at risk for an obesity level 1 and a moderate risk level of an obesity-related disease.

The width a and the height b of the abdominal area graphics may be set according to the BMI score. For example, when the BMI score is under 18.5, the user may be considered to be underweight and a proportion of the width a and the height b may be set to a ratio of 6:3. Also, when the BMI score is between 18.5 and 22.9, the user may be considered to be normal weight and the proportion of the width a and the height b may be set to a ratio of 6:4. Also, when the BMI score is between 23 and 24.9, the user may be considered to be overweight and the proportion of the width a and the height b may be set to a ratio of 6:5. Also, when the BMI score is between 25 and 29.9, the user may be considered to be obese and the proportion of the width a and the height b may be set to a ratio of 6:6. Also, when the BMI score is over 30, the user may be considered to be extremely obese and a message that a measurement is unavailable is provided.

Figure 6:
FIG. 6 is a diagram illustrating a display screen displaying anatomical area images of a contour of body fat in which body fat thickness points are linked by using a cosine interpolation, according to another embodiment of the present invention.

FIG. 6 is a diagram illustrating a display screen illustrating anatomical area images of a contour of body fat in which body fat thickness points are linked by using a cosine interpolation, according to an embodiment of the present invention.

According to an embodiment of the present invention, the contour of the body fat which is displayed on the anatomical area images may be generated using the cosine interpolation. Specifically, a graphics control unit 230 of FIG. 2 may display the body fat thickness in an envelope on the anatomical area images by generating the contour of the body fat where the body fat thickness points are linked using the cosine interpolation with respect to the body fat thickness. Also, as illustrated in FIG. 6, the anatomical area images may be rendered more realistically by using a computed tomography (CT) image, etc. Accordingly, a user may recognize a degree of obesity with respect to a predetermined anatomical area more clearly and an effect of a diet is increased.

Referring again to FIG. 2, a communication module 260 may transmit a result of a body fat measurement including the measured body fat thickness to a predetermined server such as a server of a medical institution. In this instance, the communication module 260 may support at least one of various kinds of existing access methods in association with mobile communication including a public switched telephone network (PSTN) access, a Code Division Multiple Access (CDMA), a Wideband CDMA (WCDMA), an all Internet protocol (ALL IP), a Global System for Mobile Communications (GSM), a general packet radio service (GPRS), etc. Also, the communication module 260 may support at least one protocol of call control protocols for a voice over Internet protocol (VoIP) call such as a H.323, a Message Gateway Control Protocol (MGCP), a Session Initiation Protocol (SIP) or a Media gateway control (Megaco). Also, the communication module 260 may include at least one local area communication module according to local area communication protocols such as Bluetooth, Zigbee, Infrared Data Association (IrDA), or wired/wireless LAN (WLAN), and IEEE802.11b.

The portable terminal of FIG. 2 includes a sound output unit 270 is a device for outputting various sounds. The sound output unit 270 may be, for example, a speaker, an earphone, a microphone, a built-in microphone, and the like. The sound output unit 270 may reproduce a predetermined voice specifying a body fat measurement point which is induced according to a measurement leading unit 210.

A command with respect to a local body fat measurement is inputted by a user in a user interface 280. To this end, the user interface 280 may include a keypad, a touch screen module, etc.

A display device 290 may display a display screen displaying the anatomical area images. The display device 290 may be a super twisted nematic liquid crystal display (STN LCD), a thin film transistor LCD (TFT LCD), an organic electroluminescent LCD (EL LCD), a cathode-ray tube (CRT), and a plasma display panel (PDP).

The configuration and the operation of the local body fat measurement device according to an embodiment of the present invention have been described so far. Hereinafter, a method of operating the local body fat measurement device will be described.

The method of operating the local body fat measurement device according to the present embodiment may be divided into a first example and a second example.

In the first example, a method of providing a user with anatomical area images where a measurement point is displayed includes inducing the user to measure a body fat thickness at the measurement point, and displaying the body fat thickness on the anatomical area image(s).

In the second example, the method includes, when a user selects a measurement point of a predetermined anatomical area and measures a body fat thickness, inducing a body fat measurement of at least one predetermined second measurement point, displaying each measured body fat thickness, and when displaying the measured body fat thickness with the measured thickness is impossible.

Specifically, the first example is a method of inducing the user to measure the body fat thickness at a predetermined measurement point from a start. The second example is a method in which the measurement point is selected by the user himself/herself, and the body fat thickness of the measurement point is measured. Then, whether a visual display is possible is determined based on a result of the measurement, and when the visual display is impossible, a body fat thickness measurement at a predetermined measurement point is induced like the first example. In the second example, the at least one second measurement point represents a minimum which is needed for embodying the visual display.

Hereinafter, the method of operating the local body fat measurement device according to the first embodiment will be described by referring to FIG. 7. Also, the method of operating the local body fat measurement device according to the second example will be described by referring to FIG. 8.

Figure 7:
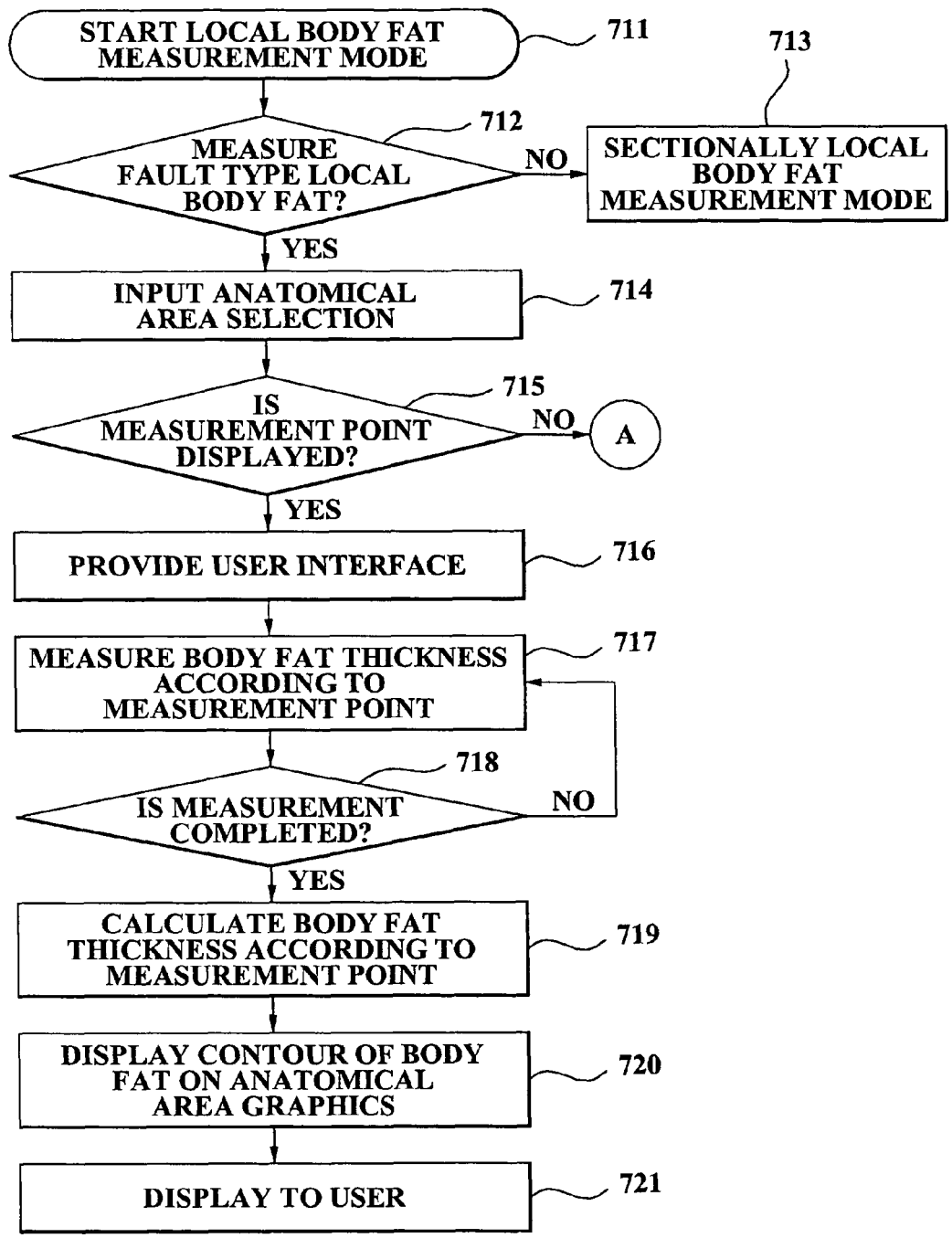
FIG. 7 is a flowchart illustrating a flow of a method of operating a local body fat measurement device according to a first example of an embodiment of the present invention.

FIG. 7 is a flowchart illustrating a flow of a method of operating a local body fat measurement device according to a first example of the present invention.

In operation 711, the local body fat measurement device according to the present embodiment converts to a local body fat measurement mode, when a command with respect to a local body fat measurement is received from a user. In operation 712, the local body fat measurement device inquires whether the local body fat measurement is a fault type local body fat measurement of the user. When the user does not select the fault type local body fat measurement, the local body fat measurement device converts to a sectionally local body fat measurement mode in operation 713. When the user selects the fault type local body fat measurement in operation 712, a selection of an anatomical area where a body fat thickness will be measured is inputted by the user in the local body fat measurement device in operation 714.

When the anatomical area is selected, the local body fat measurement device inquires whether at least one predetermined measurement point of the anatomical area is to be displayed in operation 715. In operation 715, operations when the user does not select displaying the measurement point will be described by referring to FIG. 8.

When the user selects displaying of the measurement point in operation 715, a user interface where the at least one measurement point is displayed is provided in operation 716. The user interface includes the anatomical area images corresponding to the at least one measurement point.

When the user tries to measure the body fat thickness of the measurement point according to the user interface, the local body fat measurement device measures the body fat corresponding to the measurement point in operation 717. When a body fat measurement at all measurement points is completed in operation 718, the local body fat measurement device calculates the body fat thickness of each measurement point and stores the body fat thickness measures in a predetermined memory device in operation 719.

Next, the local body fat measurement device displays a contour of a body fat on the anatomical area image(s) by using the body fat thickness measures of the each measurement point in operation 720. In operation 721, the local body fat measurement device displays the contour of the body fat to the user.

FIG. 8 is a flowchart illustrating a flow of a method of operating a local body fat measurement device according to a second example of the present embodiment.

When the user does not select the displaying the measurement point in operation 715 of FIG. 7, the local body fat measurement device measures body fat of a measurement point which is randomly selected by the user on the anatomical area in operation 811.

In operation 812, the local body fat measurement device determines whether displaying a contour of the body fat on the anatomical area image(s) is possible by using the measured body fat thickness data. When displaying the contour of the body fat is possible in operation 812, the local body fat measurement device displays the contour of the body fat on the anatomical area images in operation 817, and displays the contour of the body fat to the user in operation 818.

When displaying the contour of the body fat on the anatomical area images based on only the measured body fat thickness data is not possible in operation 812, the local body fat measurement device provides a user interface which at least one predetermined second measurement point with respect to the anatomical area is illustrated in operation 813. The user interface includes anatomical area images which the at least one second measurement point of the anatomical area is illustrated. In this instance, the at least one second measurement point represents a minimum measurement point which is needed for displaying the contour of the body fat on the anatomical area images.

When the user tries to measure the body fat at the at least one second measurement point, the local body fat measurement device measures the body fat thickness corresponding to each second measurement point in operation 814. When the body fat measurement at each second measurement point is completed in operation 815, the local body fat measurement device calculates the body fat thickness at each second measurement point and stores each body fat thickness measure in the predetermined memory device in operation 816.

Next, in operation 817, the local body fat measurement device displays the contour of the body fat on the anatomical area image(s) by using the body fat thickness which is measured in operation 811, and each body fat thickness which is measured in operation 816. In operation 818, the local body fat measurement device displays the contour of the body fat to the user.

The method of operating the local body fat measurement device according to the first example and the second example which have been described with reference to FIGS. 7 and 8 may be embodied in the configuration and the operation of the local body fat measurement device described with reference to FIGS. 1 through 6. Thus, a detailed description thereof is omitted.

The above-described methods according to the above-described embodiments of the present invention may be recorded in computer-readable media including program instructions to implement various operations embodied by a computer. The media may also include, alone or in combination with the program instructions, data files, data structures, and the like. The media and program instructions may be those specially designed and constructed for the purposes of the present invention, or they may be of the kind well-known and available to those having skill in the computer software arts. Examples of computer-readable media include magnetic media such as hard disks, floppy disks, and magnetic tape; optical media such as CD ROM disks and DVD; magneto-optical media such as optical disks; and hardware devices that are specially configured to store and perform program instructions, such as read-only memory (ROM), random access memory (RAM), flash memory, and the like. The media may also be a transmission medium such as optical or metallic lines, wave guides, etc. including a carrier wave transmitting signals specifying the program instructions, data structures, etc. Examples of program instructions include both machine code, such as produced by a compiler, and files containing higher level code that may be executed by the computer using an interpreter. The described hardware devices may be configured to act as one or more software modules in order to perform the operations of the above-described embodiments of the present invention.

In a local body fat measurement device and a method of operating the same according to the above-described embodiments provide a display screen in which a predetermined anatomical area is illustrated to a user and induces the user to measure body fat with respect to at least one measurement point of the anatomical area through the display screen, so that the user may measure a thickness of body fat of the predetermined anatomical area more conveniently.

A local body fat measurement device and a local body fat measurement method according to the above-described embodiments displays to a user a predetermined display screen that displays a contour of body fat which is generated by using a measured body fat thickness with respect to the anatomical area, so that the user may recognize the user's degree of obesity more easily, and an effect of a diet is increased.

Although a few embodiments of the present invention have been shown and described, the present invention is not limited to the described embodiments. Instead, it would be appreciated by those skilled in the art that changes may be made to these embodiments without departing from the principles and spirit of the invention, the scope of which is defined by the claims and their equivalents.

What is claimed is:

1. A method of operating a local body fat measurement device, the method comprising:
    receiving a user input as to one of a plurality of predetermined anatomical area measurement levels, the predetermined anatomical area measurement levels each indicating different measurement points and/or amounts of measurement points within a predetermined anatomical area with respect to each other;
    portraying a shape of the predetermined anatomical area as an anatomical area image and displaying at least one predetermined measurement point on the anatomical area image to the user based on the inputted predetermined anatomical area measurement level to induce the user to position the local body fat measurement device at the at least one predetermined measurement point that is based on the inputted anatomical area measurement level;
    measuring a body fat thickness of the at least one predetermined measurement point of the predetermined anatomical area;
    displaying a measured body fat thickness at each measurement point on an output device; and
    maintaining a memory device storing a local body fat measurement table storing the at least one measurement point, the local body fat measurement table including the anatomical area image portraying a shape of the predetermined anatomical area, the at least one measurement point being displayed in the anatomical area image.

2. The method of claim 1, further comprising providing a user interface inducing measurement of body fat of at least one predetermined measurement point of the anatomical area.

3. The method of claim 2, wherein the providing of the user interface comprises:
    extracting the anatomical area image, which corresponds to the predetermined anatomical area, from the memory device and displaying the extracted anatomical area image on the output device; and
    providing the user interface requesting the body fat to be measured at the measurement point.

4. The method of claim 3, wherein the displaying a measured body fat thickness indicates the body fat thickness on the anatomical area image by connecting the body fat thickness with a line.

5. The method of claim 3, wherein the displaying a measured body fat thickness indicates the body fat thickness in an envelope on the anatomical area image by using a cosine interpolation of the body fat thickness.

6. A method of operating a local body fat measurement device, the method comprising:
    receiving a user input as to one of a plurality of predetermined anatomical area measurement levels, the predetermined anatomical area measurement levels each indicating different measurement points and/or amounts of measurement points within a predetermined anatomical area with respect to each other;
    portraying a shape of the predetermined anatomical area as an anatomical area image and displaying at least one predetermined measurement point on the anatomical area image to the user based on the inputted predetermined anatomical area measurement level to induce the user to position the local body fat measurement device at the at least one predetermined measurement point that is based on the inputted anatomical area measurement level for measurement of body fat of the at least one predetermined measurement point on the predetermined anatomical area;
    measuring body fat thickness at each measurement point; and
    displaying each first fat thickness measure on anatomical area image portraying a shape of the predetermined anatomical area.

7. A method of operating a local body fat measurement device, the method comprising:

measuring body fat thickness of at least one first measurement point on a predetermined anatomical area selected by a user; and providing a user interface inducing measurement of body fat thickness of at least one predetermined second measurement point, when displaying each first body fat thickness measure, and when indicating that display of the measured thickness is impossible.

8. A computer-readable record medium storing a program for implementing the method of claim 1.

9. A local body fat measurement device comprising:

a user interface receiving a user input as to one of a plurality of predetermined anatomical area measurement levels, the predetermined anatomical area measurement levels each indicating different measurement points and/or amounts of measurement points within a predetermined anatomical area with respect to each other;

a measurement leading unit inducing measurement of body fat of at least one predetermined measurement point of the predetermined anatomical area according to the predetermined anatomical area measurement level;

a local body fat measurement unit measuring body fat thickness at each measurement point;

a graphics control unit controlling a display of each body fat thickness measure on an output device; and a memory device storing a local body fat measurement table including the at least one measurement point, wherein the local body fat measurement table comprises an anatomical area image portraying a shape of the predetermined anatomical area, and the at least one measurement point is displayed in the anatomical area image.

10. The device of claim 9, wherein the measurement leading unit extracts the anatomical area image from a memory device, displays the extracted anatomical area image on the output device, and requests the body fat thickness to be measured at the at least one measurement point illustrated in the anatomical area image through the user interface.

11. The device of claim 10, wherein a graphic control unit causes the output device to display each body fat thickness measure on the anatomical area image on the output device and, when there are plural measures, the measures are connecting by a line.

12. The device of claim 10, wherein the graphics control unit indicates the body fat thickness on the anatomical area image in an envelope using a cosine interpolation of the at least one body fat thickness measure and causes the display of the at least one measured body fat thickness on the output device.

* * * * *